United States Patent [19]

Phillip et al.

[11] 4,098,971

[45] Jul. 4, 1978

[54] ORGANOTIN POLYMERS AND ANTIFOULING PAINTS CONTAINING SAME

[75] Inventors: Arpad T. Phillip, Doncaster; Gunter Bocksteiner, Avondale Heights; Russel W. Pettis, Windsor; Geoffrey W. Glew, Caulfield, all of Australia

[73] Assignee: Commonwealth of Australia, Parkes, Australia

[21] Appl. No.: 599,859

[22] Filed: Jul. 28, 1975

Related U.S. Application Data

[63] Continuation-in-part of Ser. No. 370,443, Jun. 15, 1973, abandoned.

[30] Foreign Application Priority Data

Jul. 5, 1972 [AU] Australia .............................. 9574/72

[51] Int. Cl.$^2$ .............................................. C08F 8/44
[52] U.S. Cl. .................................... 526/16; 526/240
[58] Field of Search ................... 260/78.5 R, 78.5 T, 260/80.3 R, 80.3 N, 80 P, 80 L, 80.71, 83.5, 85.7, 86.1 R, 86.3, 86.7, 877; 526/16, 240

[56] References Cited

U.S. PATENT DOCUMENTS

| 3,167,473 | 1/1965 | Leebrick | 167/38.6 |
| 3,337,649 | 8/1967 | Black et al. | 260/877 |

FOREIGN PATENT DOCUMENTS 1,270,922  4/1972  United Kingdom.

OTHER PUBLICATIONS

Marine Fouling and its Prevention; Woodshole Oceanographic Institution, pp. 252-256.
Advances in Fouling Prevention; F. H. De La Court et al., pp. 389-391.

*Primary Examiner*—John Kight, III
*Attorney, Agent, or Firm*—Larson, Taylor and Hinds

[57] ABSTRACT

Film-forming biocidal polymers useful in marine antifouling compositions selected from copolymers of

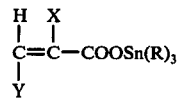

and vinyl acetate, acrylic acid and acrylamide, copolymers having the structure:

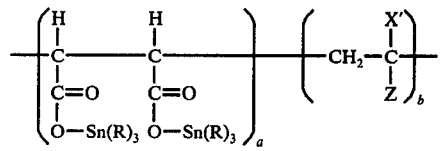

and a graft blend polymer of

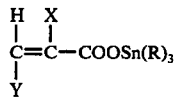

and PVC in which polymer structures X is H or CH$_3$, X' is H or CH$_3$, Y is H, —COOSn(Bu)$_3$ or —COOSn(Pr)$_3$ and Z is —COOMe.

1 Claim, No Drawings

ORGANOTIN POLYMERS AND ANTIFOULING PAINTS CONTAINING SAME

This is a continuation-in-part of application Ser. No. 370,443, filed June 15, 1973, now abandoned.

This invention relates to new trialkyltin polymers and their use in protective coating compositions, e.g. marine antifouling paints; however, the trialkyltin polymers of this invention may also be used, for example, in antifungal paints, in biocidal sealing compounds and articles (such as O-rings) in slow-release molluscicides, in insecticides or anthelmintics, and in biologically-resistant films. The invention also relates to methods of preparing trialkyltin polymers, and to protective coatings incorporating such polymers.

The polymers of the invention contain trialkyltin groups, particularly tributyltin and tripropyltin groups, which are chemically bound to a polymeric chain which preferably consists of suitably substituted film-forming molecules.

After exhaustive studies of a large variety of polymers, the following polymers have been found to be surprisingly superior materials for use in protective coating compositions:

I. Copolymers of

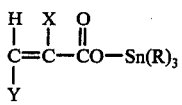

wherein
X is H or $CH_3$
Y is H, $-COOSn(Bu)_3$ or $-COOSn(Pr)_3$
R is propyl or butyl
(hereinafter referred to as "Organotin acrylate") and,
(b) vinyl acetate in a mole ration of (a) to (b) of 1:4 to 3:1, preferably about 3:1.

II. Copolymers of
(a) Organotin acrylate and
(b) acrylic acid in a mole ratio of (a) to (b) of about 1:2 to 5:1, preferably about 5:1.

III. Copolymers of
(a) Organotin acrylate and
(b) acrylamide in a mole ratio of (a) to (b) of about 3:1 to 1:3, preferably about 1:1.

IV. Copolymers having the following recurring structure:

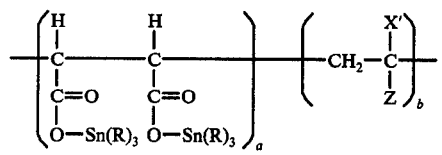

wherein R is butyl or propyl
X' is H or methyl
Z is $-COOMe$
a and b represent moles with the mole ratio of a to b being about 1:7 to 1:17, preferably about 1:1.

V. A graft blend polymer of
(a) Organotin acrylate and
(b) polyvinylchloride in a wt. ratio of about 1:10 to 1:1, preferably about 1:1.

The copolymers of groups I, II and III may be prepared by merely copolymerizing a mixture of the monomers in the defined proportions. If desired minor amounts of other monomers may be included in the mixture as long as they are not unduly detrimental to the advantageous characteristics provided by the copolymers. The polymerization may be conventionally carried out in bulk or in a suitable solvent, preferably in the presence of a free radical catalyst by heating under reflux temperatures.

The copolymer of group IV may be prepared by reacting a polymer of maleic anhydride such as a homopolymer or copolymer of maleic anhydride and a polymerizable ethylenically unsaturated monomer such as styrene with tributyltin or tripropyltin compounds containing suitable functional groups reactive with those on the polymer (e.g. tributyltin-oxide, tributyltin-methoxide), respectively. The reaction may be conducted in a suitable solvent under reflux temperature in the absence of catalyst. The graft polymer blend of group V can be prepared by reacting polyvinylchloride (PVC) with the trialkyltin acrylate or methacrylate in a suitable solvent in the presence of a free radical catalyst. Suitable solvents include polar solvents such as methyl isobutyl ketone, cellosolve acetate, diisobutyl ketone and other polar solvents suitable for dissolving polyvinyl chloride. As many of these polar solvents are expensive, and the use of some of them is restricted by environmental considerations, it is preferred to use them in admixture with aromatic solvents such as toluene, xylene and other aromatic solvents well known to persons skilled in the art.

The preferred Organotin acrylates are tributyl tin acrylate, tripropyl tin acrylate, and the corresponding methacrylates.

The proportion of organotin compound to PVC may vary from about 1:10 up to 1:1. The greater quantity of organotin compound is more effective, but it is preferred not to exceed a proportion of 1:1, beyond which the physical properties of the paint film become adversely affected. The preferred ratio is approximately 1:1 by weight.

The solution produced at the completion of this reaction is a mixture of graft polymer and mixed copolymers and will be referred to as "graft-blend copolymer". The solution so produced can be used directly for the preparation of a complete anti-fouling paint.

The trialkyltin polymers so prepared can be formulated with suitable pigments, fillers, plasticizers and other film-forming additives to produce protective coatings suitable for marine and other uses. These coatings are tough, adherent and biocidal, preventing the attachment of a wide variety of marine organisms; hence they have obvious applications as marine antifouling paints for the underwater areas of ship's hulls, submerged structures such as buoys, piers, etc. Physical properties of the film (e.g. chemical resistance, solubility, toughness, adhesion, flexibility) ma be varied by selection of appropriate combinations of the groups X, Y and Z.

It will be understood that the present applicants do not wish to be restricted by the following or any hypothetical mechanism postulated for the biocidal effectiveness of these compositions. However, it is believed that release of toxic organotin compounds is effected by reaction with sea water in the following manner:

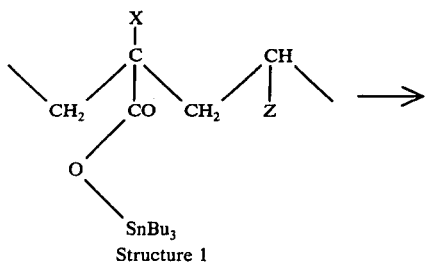

Structure 1

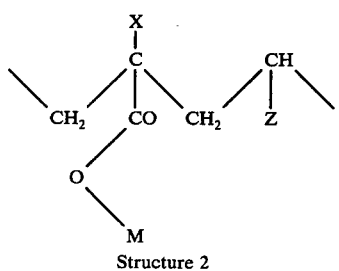

Structure 2 where
M = H, Na, K or other cations.
Z = OAc, COOH and CONH$_2$
X = H or Me.

By a suitable choice of functional groups, X, Y and Z the rate of reaction with sea water can be controlled to produce structure 2, so that the toxic release rate is regulated at about 5 to 20 mg/m$^2$/day. (i.e. 5 to 20 milligrams of tin compound per square meter of paint surface per day), preferably about 12 mg/m$^2$/day.

The principal advantages of the trialkyltin polymers of this invention over existing materials presently in use are:

(i) they are highly toxic to a wide range of sessile or encrusting marine organisms, such as barnacles, tube worms, bryozoans, ascidians, hydroids and certain species of algae.

(ii) they have a controlled release of the toxic groups from the polymers, which undergo a complex series of chemical reactions when immersed in sea water.

(iii) they are not toxic to man when handled with normal care either in the solid form or in solution; this is due to the fact that the toxic groups are chemically bound to the polymer and normally are not released until the polymer is immersed in sea water.

(iv) they are not dangerous as pollutants of the marine environment because the toxic trialkyltin compounds released from the polymers are readily degraded to harmless tin salts in the sea water.

(v) they are non-corrosive to steel, and hence these polymers can be used for protective coatings without the need for extensive barrier or anticorrosive coatings on steel.

(vi) they are more effective in preventing the attachment of fouling organisms to immersed surfaces because the toxic release rate (i.e. the rate of release of the toxic organotin groups) can be controlled to the minimum level (falling within the range 5 to 20 mg/m$^2$/day), the toxic concentration of trialkyltin groups in the trialkyltin polymer can be made very high (up to 80% by weight and preferably a minimum of 30% by weight), and the toxic release is not affected by allowing the paint surface to dry out, as in docking procedures; these properties have considerable importance for shipping since the interval between dry-docking can be extended for periods up to three years and since repainting is not essential during intermediate dockings.

The following Examples relate to the preparation of trialkyltin polymers according to the invention, and to the preparation of marine antifouling paints based thereon.

In the Examples, tributyltin compounds have been preferred since these have the optimum balance between high toxicity to marine organisms and tolerable toxicity to man. The Examples described give typical procedures for the preparation of trialkyltin polymers of the five groups I through V described above and also for the preparation of long-lasting antifouling paints derived from these polymers.

TRIALKYLTIN POLYMERS

EXAMPLE 1 (COPOLYMER)

A mixture of tributyltin acrylate (72g) styrene (11.6g) and acrylonitrile (10.6g) dissolved in chloroform (100 ml) was heated under reflux in the presence of azobis (isobutyronitrile) (0.94g) and acetic acid (0.09g) for a period of 5 hrs. After removal of the solvent in vacuum, a hard, brittle solid was obtained.

EXAMPLE 2 (COPOLYMER)

A bulk polymerization was carried out by heating tributyltin acrylate (108g., 0.3 moles), vinyl acetate (8.6g., 0.1 mole) and benzoyl peroxide (1.1g) under reflux at 80° C for a period of 2 hours. Upon cooling, a clear slightly elastic solid was obtained; it was soluble in toluene, xylene or methyl isobutylketone.

EXAMPLE 3 (COPOLYMER)

A mixture of tributyltin acrylate (36g., 0.1 mole), vinyl acetate (34.4g., 0.4 moles) and benzoyl peroxide (0.7g) was bulk polymerized at 80° C during a period of 2 hours. A translucent, hard polymer was obtained by cooling the reaction mixture.

EXAMPLE 4 (COPOLYMER)

Tributyltin acrylate (36g., 0.1 mole) and acrylic acid (7.2g., 0.1 mole) were bulk polymerized using benzoyl peroxide (0.4 g) and heating at 80° for a period of 0.5 hours. An exothermic reaction took place and a hard, brittle solid was readily formed within the reaction period. This polymer can be milled into a smooth white powder which is insoluble in most organic solvents, but partially soluble in water; however, the white powder can be added to film-forming polymers and may then serve as a toxic, controlled-release pigment.

EXAMPLE 5 (COPOLYMER)

A bulk polymerization was performed with tributyltin acrylate (108g., 0.3 moles) vinyl acetate (8.6g., 0.1 mole) and maleic anhydride (9.8g., 0.1 mole), using benzoyl peroxide (1.25 g) as catalyst at 80° for a period of 2 hours. This polymer is soluble in toluene and xylene and has improved adhesion and film-forming properties.

EXAMPLE 6 (GRAFT POLYMER)

Polyvinyl chloride, of the type used as commercial coating resins (50g) and tributyltin acrylate (50g) dissolved in a solvent mixture of toluene (50 ml) and methyl isobutylketone (50 ml) were heated in the presence of benzoyl peroxide (1.0g) at 80° C for a period of 3 hours; the mixture was stirred continuously during the polymerization stage. A viscous, pale yellow solution was produced at the completion of this reaction, which gave a mixture of graft polymer and mixed copolymers. The solution can be used directly for the preparation of a complete antifouling paint.

EXAMPLE 7 (CHEMICALLY-MODIFIED POLYMER)

A copolymer (50g) of styrene and maleic anhydride, containing an 8:1 molar ratio of monomers, was dissolved in the minimum volume of toluene and caused to react with bis(tributyltin) oxide (50g): the reaction was completed by heating the solution under reflux for 2 hours. The solvent was distilled under vacuum in order to isolate the organotin polymer, which was purified by repeated washing in hexane. The pure polymer was isolated as a translucent, slightly flexible solid, still containing 5 to 10% of the original maleic anhydride groups.

EXAMPLE 8 (COPOLYMER)

A mixture of tripropyltin acrylate (96g) and vinyl acetate (8.6g) was heated at 80° with the free radical initiator, benzoyl peroxide (1g) for a period of 2 hours. Upon cooling the flask, a slightly cloudy polymeric solid was obtained; this material is soluble in methyl isobutylketone.

EXAMPLE 9 (PREPARATION OF GRAFT-BLEND POLYMER)

A commercial grade of polyvinyl chloride resin (2.6 kg) as commonly used in surface coatings, and tributyltin acrylate (2.7 kg) are dissolved in a solvent mixture consisting of xylol (1.3 kg) methyl isobutylketone (0.6 kg) and cellusolve acetate (4.5 kg) by means of stirring and heating to 80° C. When a homogeneous mixture is obtained, the polymerization catalyst benzoyl peroxide (50 g) is added at 80° C in two 25g portions. The first portion is added at the formation of the homogeneous solution, the second portion at 2 to 3 hours later. The total period of polymerization at 80° C must be at least 6 hours with continuous stirring, so that all of the monomer, tributyltin acrylate, has been polymerized. The completion of polymerization can be readily determined by an infrared absorption spectrum of the polymeric products.

The resulting pale yellow, viscous solution can be used directly in the preparation of antifouling paints. Some additional solvent mixture, consisting of xylol (0.6 kg), methyl isobutylketone (0.3 kg) and cellusolve acetate (2.2 kg) is added to the warm solution in order to keep the polymers in solution on cooling to room temperature.

EXAMPLE 10 (PREPARATION OF GRAFT-BLEND POLYMER)

The above polymerization may be carried out with identical quantities of polyvinyl chloride and tributyltin acrylate dissolved in di-isobutyl ketone (6.4 kg) as solvent. The final polymer solution is diluted with a further quantity of solvent (2.8 kg) to produce a clear, viscous solution on cooling.

EXAMPLE 11 (PREPARATION OF GRAFT-BLEND POLYMER)

Commercial grade polyvinyl chloride, (2.6 kg) suitable for use in surface coatings and tripropyltin acrylate (1.8 kg) are dissolved in di-isobutyl ketone (6.0 kg) by means of stirring and heating to 80° C. When a homogeneous mixture is obtained, the polymerization catalyst, benzoyl peroxide is added in two portions, the first portion (25 g) at the formation of a homogeneous solution and the second portion (25 g) at 2 to 3 hours later. The total period required for polymerization must be at least 6 hours at 80° C, with continuous stirring. The resulting pale yellow solution may be diluted with a further quantity of di-isobutylketone (3.0 kg) to keep the polymers in solution at room temperature.

EXAMPLE 12

The tributyltin polymer prepared in Example 7 was used to prepare the following antifouling paint by ball-milling the components for a period of 6 hours:
Tributyltin Polymer (as in Example 7) : 50 g
Toluene : 25 g
Methyl Isobutyl ketone : 25 g
Cuprous oxide (red) : 60 g This paint was applied by spray-painting on to a steel plate previously coated with a protective anti-corrosive paint based on an aluminum pigmented, bituminous resin. The adhesion of the film was excellent and the antifouling action was highly effective against visible macrofouling organisms.

EXAMPLE 13

An effective coating was prepared from the components listed below:
Tributyltin Polymer (as in Example 2) : 60 g
Cuprous oxide (red) : 172 g
Toluene : 60 g This mixture was ball-milled for a period of 4 hours, until fineness of grind reached a particle size of less than 25 microns. A panel coated with this antifouling paint has prevented the attachment of visible sessile and encrusting marine organisms during a period of 22 months immersion in Sydney harbour; the testing is still continuing.

EXAMPLE 14

A copolymer was prepared as in Example 4, using tributyltin acrylate and acrylic acid in a molar ratio of 5:1 (for example, a weight of 36 g : 1.5 g respectively).
The antifouling paint was prepared as follows:
Tributyltin Polymer (prepared as above) : 40 g
Cuprous oxide (red) : 60 g
Toluene : 50 g
Methyl Isobutylketone: 50 g After ball-milling the mixture for 4 hours, the paint was applied to test panels, which were free of visible macrofouling organisms after 15 months of immersion in Sydney harbour.

EXAMPLE 15

The following components were ball-milled for a period of 4 hours:
Tributyltin polymer (as in Example 6) : 30 g
Cuprous oxide : 100 g Xylol : 50 g
Methyl Isobutylketone : 80 g This coating has shown excellent antifouling properties during a period of 20 months immersion in Sydney harbour.

EXAMPLE 16

The following Example illustrates the preparation of a white antifouling paint which utilizes an organotin polymer without the presence of cuprous oxide.

Tributyltin polymer (as in Example 6) : 30 g
Titanium dioxide : 70 g
Triazine herbicide ("ametryne") : 10 g
Toluene : 60 g
Methyl isobutyl ketone : 40 g The above components were ball-milled for 6 hours and the resulting paint was applied by spray-painting to steel panels, previously coated with an aluminum-bituminous anticorrosive paint. This panel was immersed in Sydney harbour for a period of 6 months, during which no visible marine fouling organisms were attached, except for a thin film of slime.

EXAMPLE 17

The following Example represents the preparation of a green antifouling paint, which utilizes the organotin polymer as the sole toxic agent and incorporates chromium (III) oxide as an inert pigment.

Tributyltin graft polymer (as in Example 6) : 30 g
Chromium (III) oxide (type GX) : 87 g
Xylene : 60 g
Methyl isobutyl ketone : 40 g After the above mixture was ball-milled for a period of 6 hours, the paint was applied to test panels which were subsequently immersed in the sea at Williamstown. After 12 months immersion, the panel was still free of visible macrofouling organisms.

EXAMPLE 18

A tough adherent antifouling coating can be prepared from the tripropyltin acrylate copolymer using the following components:

Tripropyltin polymer as in Example 8 : 30 g
Cuprous oxide (red) : 98 g
Methyl isobutyl ketone : 35 g The above mixture was ball-milled for a period of 2 hours, so that the fineness of grind attained particle size of less than 25 microns. The composition is suitable for application by brush or can be diluted with toluene (35 grams) to produce a consistency suitable for spray painting.

EXAMPLE 19 (PREPARATION OF ANTIFOULING PAINT)

Graft-blend polymer (as in Example 12) : 197 g
Cuprous oxide : 657 g
Ametryne : 98 g
Di-isoburyl ketone : 48 g The above components were mixed in a ball-mill and ground for a period of 4 hours, until the fineness of grind reached a particle size of less than 25 microns. A panel coated with this antifouling paint has prevented the attachment of all visible fouling organisms, including the marine slime film, during a period of 24 months immersion in Sydney harbour.

EXAMPLE 20 (PREPARATION OF ANTIFOULING PAINT)

Graft-blend polymer solution (as in Example 9) : 14.8 kg
Cuprous oxide : 17.7 kg
Diuron : 1.3 kg
Xylol : 0.7 kg
Cellusolve acetere : 2.6 kg
Methyl isobutyl ketone : 0.4 kg The above components were ball-milled for 6 hours and the resulting paint was applied by spray-painting to steel panels, previously coated with an anticorrosive primer. The panel has been immersed in Sydney harbour for a period of 24 months, during which no visible marine fouling organisms had attached to the surface.

FIGS. 1 and 2 of the accompanying drawings show infrared absorption spectra of the copolymers of this invention. In the drawings "% T" = "% Transmission" and "cm$^{-1}$" refers to the wavelength.

FIG. 1 shows the infrared absorption spectrum of the copolymer tributyltin acrylate-styrene-acrylonitrile (referred to in Example 1), and indicates:
poly(acrylonitrile) absorption at 2253 cm$^{-1}$
poly(styrene) absorption at 3042, 1602 and 702 cm$^{-1}$
poly(tributyltin acrylate) absorption at 2930, 2860 and 1645 cm$^{-1}$.

FIG. 2 shows infrared absorption spectrum of the copolymer tributyltin acrylate-vinyl acetate (referred to in Example 2), and indicates:
poly(vinyl acetate) absorption at 1728 cm$^{-1}$
poly(tributyltin acrylate) absorption at 2930, 2860 and 1640 cm$^{-1}$.

It is claimed:

1. A film-forming antifouling agent consisting essentially of an organotin containing copolymer, which is composed of:

(a) a recurring organotin moiety consisting of:

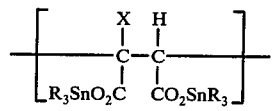

wherein R is a member selected from the class consisting of propyl and butyl; X is a member selected from the class consisting of hydrogen and methyl;

(b) recurring units of at least one comonomer selected from the group consisting of vinyl acetate, acrylic acid and acrylamide.

* * * * *